United States Patent
Park et al.

(10) Patent No.: US 11,497,421 B2
(45) Date of Patent: Nov. 15, 2022

(54) DEVICE AND METHOD FOR SPECTRUM ANALYSIS AND DEVICE FOR BLOOD GLUCOSE MEASUREMENT

(71) Applicant: SAMSUNG ELECTRONICS CO., LTD., Suwon-si (KR)

(72) Inventors: Yun S Park, Suwon-si (KR); Sang Kon Bae, Seongnam-si (KR); So Young Lee, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 394 days.

(21) Appl. No.: 16/739,421

(22) Filed: Jan. 10, 2020

(65) Prior Publication Data

US 2020/0146597 A1 May 14, 2020

Related U.S. Application Data

(62) Division of application No. 15/426,555, filed on Feb. 7, 2017, now Pat. No. 10,561,348.

(30) Foreign Application Priority Data

Sep. 5, 2016 (KR) .......................... 10-2016-0114062

(51) Int. Cl.
  *A61B 5/1455* (2006.01)
  *A61B 5/145* (2006.01)
  *A61B 5/00* (2006.01)

(52) U.S. Cl.
  CPC ........ *A61B 5/14532* (2013.01); *A61B 5/0075* (2013.01); *A61B 5/7221* (2013.01)

(58) Field of Classification Search
  CPC ... A61B 5/0205; A61B 5/0075; A61B 5/1455; A61B 5/14551; A61B 5/14552;
  (Continued)

(56) References Cited

U.S. PATENT DOCUMENTS 4,655,225 A * 4/1987 Dahne ................ A61B 5/14532
  600/316
5,372,135 A * 12/1994 Mendelson ........ A61B 5/14532
  600/316

(Continued)

FOREIGN PATENT DOCUMENTS

JP     2013-110390 A    6/2013
KR    10-0389590 B1    6/2003
(Continued)

OTHER PUBLICATIONS

Anonymous, "Story about statistics using Minitab #1 (mean, variance, standard deviation, histogram, boxplot)", http://blog.minitab.co.kr/130152643699, Nov. 26, 2012, total 10 pages.

*Primary Examiner* — Chu Chuan Liu
(74) *Attorney, Agent, or Firm* — Sughrue Mion, PLLC

(57) ABSTRACT

A device and method for spectrum analysis in which differences among skin spectra are quantitatively analyzed, and a blood glucose measurement device are provided. The device for spectrum analysis includes an obtainer configured to acquire a plurality of skin spectra; and a processor configured to generate a plot of difference degree of spectra which represents differences among the acquired plurality of skin spectra, and determine whether the plurality of skin spectra are appropriate for blood glucose measurement based on the plot of difference degree of spectra.

11 Claims, 17 Drawing Sheets

(58) Field of Classification Search
CPC ... A61B 5/14532; A61B 5/1495; A61B 5/721; A61B 5/7221
See application file for complete search history.

(56) References Cited

U.S. PATENT DOCUMENTS

| | | |
|---|---|---|
| 5,945,676 A | 8/1999 | Khalil et al. |
| 6,115,673 A | 9/2000 | Malin et al. |
| 6,309,884 B1 | 10/2001 | Cooper et al. |
| 6,587,702 B1 | 7/2003 | Ruchti et al. |
| 6,919,566 B1 | 7/2005 | Cadell |
| 8,326,404 B2 | 12/2012 | Zeng et al. |
| 8,386,187 B2 | 2/2013 | Otvos |
| 9,103,793 B2 | 8/2015 | Bechtel et al. |
| 9,883,833 B2 | 2/2018 | Barnes et al. |
| 10,060,794 B2 | 8/2018 | Lee |
| 10,278,625 B2 | 5/2019 | Shimizu et al. |
| 2002/0038080 A1 | 3/2002 | Makarewicz et al. |
| 2006/0063993 A1* | 3/2006 | Yu .................... A61B 5/14532 600/322 |
| 2006/0167348 A1 | 7/2006 | Arnold et al. |
| 2013/0109278 A1 | 5/2013 | Kimba |
| 2013/0197332 A1 | 8/2013 | Lucisano et al. |
| 2016/0061810 A1 | 3/2016 | Kim et al. |
| 2016/0097716 A1 | 4/2016 | Gulati et al. |
| 2017/0079565 A1 | 3/2017 | Choi et al. |

FOREIGN PATENT DOCUMENTS

| | | |
|---|---|---|
| KR | 10-2011-0086074 A | 7/2011 |
| KR | 10-2014-0082642 A | 7/2014 |
| KR | 10-2016-0028229 A | 3/2016 |
| KR | 10-2017-0035675 A | 3/2017 |

\* cited by examiner

DEVICE AND METHOD FOR SPECTRUM ANALYSIS AND DEVICE FOR BLOOD GLUCOSE MEASUREMENT

CROSS-REFERENCE TO RELATED APPLICATION(S)

This application is a Divisional Application of U.S. application Ser. No. 15/426,555, filed Feb. 7, 2017, which claims priority from Korean Patent Application No. 10-2016-0114062, filed on Sep. 5, 2016 in the Korean Intellectual Property Office, the entire disclosure of which is incorporated herein by reference for all purposes.

BACKGROUND

1. Field

Apparatuses and methods consistent with exemplary embodiments relate skin spectrum analysis.

2. Description of Related Art

A spectrum is generally used to observe a rainbow of colors in visible light when separated using a tool, such as a prism. In a broad sense, a spectrum applies to any technology which decomposes a complex signal with one or two signals and provides a graphical representation of the signal.

Recently, a method of analyzing properties of an object by analyzing a spectrum of light transmitted through the object for a specific period of time has been studied. In the case of an infrared spectrum, it can be used in most conditions, such as gases, liquids, crystals, amorphous solids, polymers and solutions, and can be widely applied to the identification, qualitative or quantitative analysis of compounds.

In order to improve the accuracy of spectrum-based analysis, it is important to select the spectrum to be used for analysis so that the spectrum does not contain information (e.g., noise) other than the information required for analysis. Whether or not the spectrum measured for a specific period of time contains information other than the information necessary for analysis is determined based on whether or not the similarity between spectra is high. Therefore, it is necessary to accurately measure the similarity between spectra.

SUMMARY

Exemplary embodiments provide a device and method for spectrum analysis in which differences among skin spectra are quantitatively analyzed, and a blood glucose measurement device.

According to an aspect of an exemplary embodiment, there is provided a device for spectrum analysis including: an obtainer configured to acquire a plurality of skin spectra; and a processor configured to generate a plot of difference degree of spectra which represents differences among the acquired plurality of skin spectra, and determine whether the plurality of skin spectra are appropriate for blood glucose measurement based on the plot of difference degree of spectra.

The processor may generate a noise distribution graph based on the plot of difference degree of spectra, extract a percentile score that corresponds to a predetermined percentile in the generated noise distribution graph, and compare the extracted percentile score with a first reference value to determine whether the plurality of skin spectra are appropriate for blood glucose measurement.

When the extracted percentile score is equal to or smaller than the first reference value, the processor may determine that the plurality of skin spectra are appropriate for blood glucose measurement.

The predetermined percentile may be a 95 percentile or a 99 percentile.

The percentile score may be a noise value which corresponds to the predetermined percentile in the generated noise distribution graph.

The first reference value may be determined according to a state of a subject at the time of measurement of the plurality of skin spectra.

The processor may convert the plot of difference degree of spectra into frequency domain by performing a fast Fourier transform (FFT) and determine whether the plurality of skin spectra are appropriate for blood glucose measurement by comparing a second reference value with a ratio of a sum of amplitude absolute values in a predetermined frequency domain of the converted plot of difference degree of spectra and a sum of amplitude absolute values over an entire frequency domain.

When the ratio of the sum of amplitude absolute values in a predetermined frequency domain and the sum of amplitude absolute values over an entire frequency domain is equal to or smaller than the second reference value, the processor may determine that the plurality of skin spectra are appropriate for blood glucose measurement.

The processor may calculate a noise value by performing baseline fitting on two spectra and then integrating a difference in frequency intensity between the two spectra and generates the plot of difference degree of spectra based on the calculated noise value.

When it is determined that the plurality of skin spectra are inappropriate for blood glucose measurement, the obtainer may acquire an additional skin spectrum.

According to an aspect of another exemplary embodiment, there is provided a method of spectrum analysis including: acquiring a plurality of skin spectra; generating a plot of difference degree of spectra which represents differences among the acquired plurality of skin spectra; and determining whether the plurality of skin spectra are appropriate for blood glucose measurement based on the plot of difference degree of spectra.

The determination may include: generating a noise distribution graph based on the plot of difference degree of spectra; extracting a percentile score which corresponds to a predetermined percentile in the generated noise distribution graph; and comparing the extracted percentile score with a first reference value and determining whether the plurality of skin spectra are appropriate for blood glucose measurement based on a comparison result.

The determination based on the comparison result may include, when the extracted percentile score is equal to or smaller than the first reference value, determining that the plurality of skin spectra are appropriate for blood glucose measurement.

The predetermined percentile may be a 95 percentile or a 99 percentile.

The percentile score may be a noise value which corresponds to the predetermined percentile in the generated noise distribution graph.

The first reference value may be determined according to a state of a subject at the time of measurement of the plurality of skin spectra.

The determination may include: converting the plot of difference degree of spectra into frequency domain by performing a fast Fourier transform (FFT); comparing a second reference value with a ratio of a sum of amplitude absolute values in a predetermined frequency domain of the converted plot of difference degree of spectra and a sum of amplitude absolute values over an entire frequency domain; and determining whether the plurality of skin spectra are appropriate for blood glucose measurement based on a comparison result.

The determination based on the comparison result may include, when the ratio of the sum of amplitude absolute values in a predetermined frequency domain and the sum of amplitude absolute values over an entire frequency domain is equal to or smaller than the second reference value, determining that the plurality of skin spectra are appropriate for blood glucose measurement.

The generation may include: calculating a noise value by performing baseline fitting on two spectra and then integrating a difference in frequency intensity between the two spectra, and generating the plot of difference degree of spectra based on the calculated noise value.

The method may further include acquiring an additional skin spectrum when it is determined that the plurality of skin spectra are inappropriate for blood glucose measurement.

According to an aspect of another exemplary embodiment, there is provided a device for blood glucose measurement including: a spectroscope configured to emit light onto a subject and acquire a plurality of skin spectra based on light passing through or reflected from the subject; a first analyzer configured to generate a plot of difference degree of spectra which represents differences among the acquired plurality of skin spectra, and determine whether the plurality of skin spectra are appropriate for blood glucose measurement based on the plot of difference degree of spectra; and a blood glucose measurer configured to perform blood glucose measurement using a plurality of skin spectra which are determined as being appropriate for blood glucose measurement.

The first analyzer may generate a noise distribution graph based on the plot of difference degree of spectra, extract a percentile score that corresponds to a predetermined percentile in the generated noise distribution graph, and compare the extracted percentile score with a first reference value to determine whether the plurality of skin spectra are appropriate for blood glucose measurement.

When the extracted percentile score is equal to or smaller than the first reference value, the first analyzer may determine that the plurality of skin spectra are appropriate for blood glucose measurement.

The first analyzer may convert the plot of difference degree of spectra into frequency domain by performing a fast Fourier transform (FFT) and determine whether the plurality of skin spectra are appropriate for blood glucose measurement by comparing a second reference value with a ratio of a sum of amplitude absolute values in a predetermined frequency domain of the converted plot of difference degree of spectra and a sum of amplitude absolute values over an entire frequency domain.

When the ratio of the sum of amplitude absolute values in a predetermined frequency domain and the sum of amplitude absolute values over an entire frequency domain is equal to or smaller than the second reference value, the first analyzer may determine that the plurality of skin spectra are appropriate for blood glucose measurement.

The first analyzer may calculate a noise value by performing baseline fitting on two spectra and then integrating a difference in frequency intensity between the two spectra and generate the plot of difference degree of spectra based on the calculated noise value.

The spectroscope may emit near-infrared light and acquires near-infrared extinction spectrum absorbed by the subject.

The device may further include a sensor configured to measure an environmental index including at least one of a temperature, humidity and a degree of motion of the blood glucose measurement device during the acquisition of the skin spectra; a second analyzer configured to analyze a correlation between the environmental index and an overall similarity of skin spectra; and an output unit configured to output a predetermined warning signal during additional acquisition of a skin spectrum when an environmental index having a positive correlation with the overall similarity of skin spectra is equal to or smaller than a third reference value, or when an environmental index having a negative correlation with the overall similarity of skin spectra is equal to or greater than a fourth reference value.

When it is determined that the plurality of skin spectra are inappropriate for blood glucose measurement, the spectroscope may acquire an additional skin spectrum.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
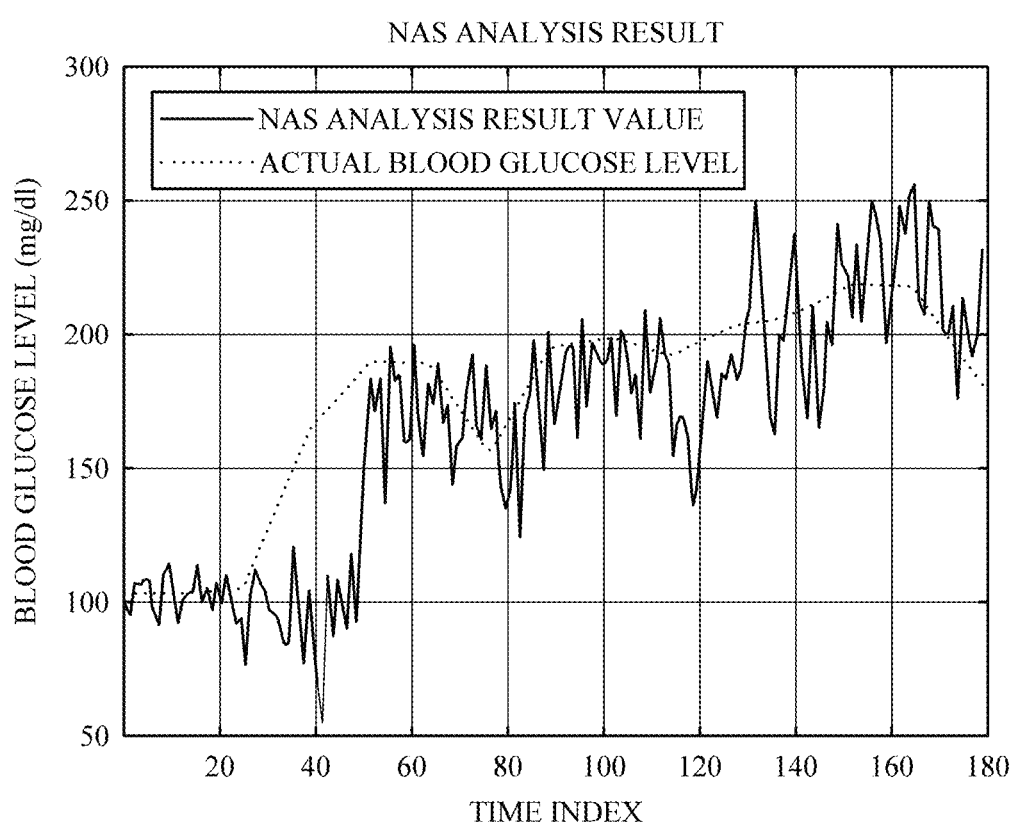
FIG. 1 is a graph illustrating an example of a net analyte signal (NAS) analysis result in the case of skin spectra showing a high overall similarity.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The terms "comprises", "comprising", "includes" and/or "including" as used herein will be understood to mean that the list following is non-exhaustive and may or may not include any other additional suitable items, for example one or more further component(s), operation(s), procedure(s), and/or element(s) as appropriate. According to various exemplary embodiments of the present disclosure, the term "unit", means, but is not limited to, a software or hardware component, such as a Field Programmable Gate Array (FPGA) or Application Specific Integrated Circuit (ASIC), which performs certain tasks. A "unit" may advantageously be configured to reside on the addressable storage medium and configured to be executed on one or more processors.

Thus, a "unit" may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The components and the functionality provided for the units may be combined into fewer components and units or further separated into additional components and units.

Figure 2:
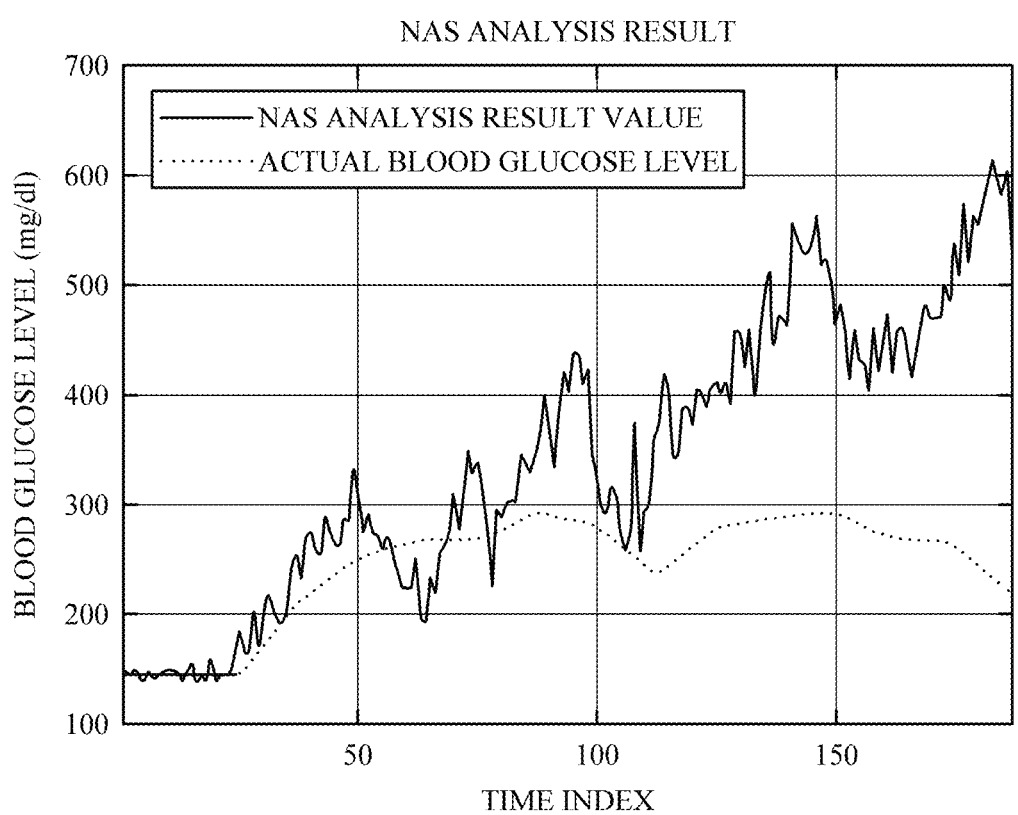
FIG. 2 is a graph illustrating an example of a NAS analysis result in the case of skin spectra showing a low overall similarity.

FIG. 1 is a graph illustrating an example of a net analyte signal (NAS) analysis result in the case of skin spectra showing a high overall similarity, and FIG. 2 is a graph illustrating an example of a NAS analysis result in the case of skin spectra showing a low overall similarity. Herein, the overall similarity of skin spectra is a numerical value that represents the whole similarity among a plurality of skin spectra.

FIGS. 1 and 2 show both NAS analysis results of skin spectra and actual blood glucose levels. The NAS analysis results of FIGS. 1 and 2 may be obtained by applying an NAS algorithm to skin spectra. The actual blood glucose levels of FIGS. 1 and 2 are obtained by analyzing blood samples taken from a subject. For example, the actual blood glucose levels may be acquired using an electrochemical method for measuring current due to electrons produced during the reaction between glucose in the blood with enzyme, or a photometric method for measuring the color from enzyme reaction.

When comparing the graphs of FIG. 1 and FIG. 2, it can be seen that the difference between the NAS analysis result and the actual blood glucose level in FIG. 2 is relatively larger than the difference in FIG. 1. In addition, the blood glucose level in FIG. 1 is in a range between 50 and 300 mg/dl, whereas the blood glucose level in FIG. 2 is in a range between 100 and 700 mg/dl, and hence it can be understood that the difference between the NAS analysis result and the actual blood glucose level in FIG. 2 is considerably larger than the difference in FIG. 1. One of the factors causing the significant difference between the NAS analysis result and the actual blood glucose level in FIG. 2 may be skin spectra having a low overall similarity which are used in the NAS analysis, and there may also be other various factors, such as temperature, humidity, and food intake by a subject during the measurement of the skin spectra.

As shown in FIG. 1, in the case of blood glucose measurement using skin spectra showing a high overall similarity, it can be viewed that the NAS analysis result and the actual blood glucose level are likely to be similar to each other. However, in the case of blood glucose measurement using skin spectra showing a low overall similarity, a significant discrepancy between the NAS analysis result and the actual blood glucose level occurs, as shown in FIG. 2, so that it may be inappropriate to use the NAS analysis result in blood glucose measurement.

Figure 3:
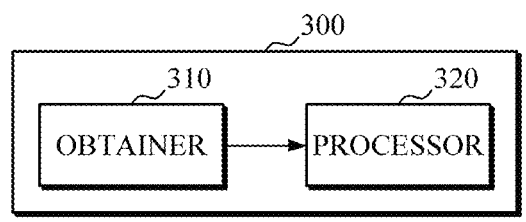
FIG. 3 is a block diagram illustrating a device for spectrum analysis according to an exemplary embodiment.

FIG. 3 is a block diagram illustrating a device for spectrum analysis according to an exemplary embodiment.

Referring to FIG. 3, the device 300 for spectrum analysis includes an obtainer 310 and a processor 320.

The obtainer 310 may obtain a plurality of skin spectra. For example, the obtainer 310 may acquire skin spectra through a spectroscope directly/indirectly connected with the device 300 or may acquire skin spectra from a storage device, such as a portable storage device, through a wired/wireless communication device. In this case, the skin spectra acquired by the obtainer 310 may be extinction spectra, transmission spectra, or reflective spectra.

The processor 320 may generate a plot of difference degree of spectra which represents differences among the acquired plurality of skin spectra. More specifically, the processor 320 may calculate a noise value between every two of the plurality of skin spectra and generate the plot of difference degree of spectra using the calculated noise values. In this case, the noise value between a specific skin spectrum and another skin spectrum has a positive correlation with a difference between the two skin spectra and has a negative correlation with a similarity between the two spectra. Therefore, when the noise value is small, the difference between a specific skin spectrum and another skin spectrum is assumed to be small and the similarity between the two skin spectra is high.

For example, the processor 320 may calculate the noise value between every two of the plurality of skin spectra using Equation 1 below.

$$\text{Noise value} = \frac{\text{Area between two spectra}}{\text{Area of reference spectrum}} \quad (1)$$

Here, the reference spectrum may be a spectrum associated with a reference blood glucose level (e.g., skin spectrum when the glucose level is 100 mg/dl).

The area of the reference spectrum may be obtained by performing mean centering on the reference spectrum. More specifically, since the process of mean centering is performed to calculate a difference between each variable and an average value, the area of the reference spectrum may be obtained by calculating the mean of frequency intensity of the reference spectrum and then integrating a difference and the mean and the frequency intensity of the reference spectrum. In addition, the area between the two spectra may be obtained by performing baseline fitting on the two spectra and then integrating a difference in frequency intensity between the two spectra.

The processor 320 may calculate the noise value between every two of the plurality of spectra and generate the plot of difference degree of spectra that visually represents the noise values. For example, the processor 320 may calculate a noise value between a skin spectrum measured at a point in time that corresponds to an X-axis value and a skin spectrum measured at a point in time that correspond to a Y-axis value. The processor 320 may generate the plot of difference degree of spectra using the calculated noise value.

The processor 320 may quantitatively analyze the plot of difference degree of spectra so as to determine whether the plurality of skin spectra are appropriate for the blood glucose measurement. The device 300 for spectrum analysis may quantitatively analyze the plot of difference degree of spectra which shows differences among the plurality of skin spectra, thereby making accurate and efficient determination based on objective criteria. In addition, since the device 300 is able to quantify the overall similarity of skin spectra by quantitatively analyzing the plot of different degree of spectra, it may be possible to perform high-speed analysis and large-scale analysis through a computer, a processor, an automation device, or the like.

According to an exemplary embodiment, the processor 320 may generate a noise distribution graph based on the plot of difference degree of spectra and determine whether the plurality of skin spectra are appropriate for blood glucose measurement based on the generated noise distribution graph.

In more detail, the processor 320 may count the number of points at which the noise values are identical in the plot of difference degree of spectra and may generate the noise distribution graph based on the counted number. In addition, the processor 320 may extract a percentile score that corresponds to a specific percentile in the generated noise distribution graph, compare the extracted percentile score with a first reference value, and, when the extracted percentile score is equal to or smaller than the first reference value, determine that the plurality of skin spectra are appropriate for blood glucose measurement. In this case, the percentile may indicate a point out of 100 points that equally divide data which are arranged in size order. In addition, the percentile score is a point that corresponds to a specific percentile, indicating a noise value that corresponds to the specific percentile. The extracted percentile score may be assumed to be a value that has a negative correlation with the overall similarity of the skin spectra.

The first reference value may be determined according to a state of the subject at the time of measurement of the plurality of skin spectra. For example, if the first reference value is set to "10" (the value can be set differently) for the subject on empty stomach at the time of measuring the skin spectra, the first reference value may be set to be greater than "10" for the case where food or glucose intake by the subject is not taken into consideration or for the case of the subject's intake of glucose for an oral glucose tolerance test (OGTT). This considers that the percentile score extracted based on the skin spectra that are measured while the subject is taking food or glucose can be relatively high compared to when measured in a fasting state of the subject. Information about whether or not the subject has taken food or glucose or the amount of intake thereof may be manually input by a user or may be acquired from a biometric recognition apparatus capable of detecting the subject's intake of food or glucose.

According to another exemplary embodiment, the processor 320 may convert the plot of difference degree of spectra into frequency domain and determine whether the plurality of skin spectra are appropriate for blood glucose measurement based on the converted plot of difference degree of spectra.

More specifically, the processor 320 may convert the plot of difference degree of spectra in time domain into frequency domain using a fast Fourier transform (FFT). In addition, based on the converted plot of difference degree of spectra, the processor 320 may determine whether the plurality of skin spectra are appropriate for blood glucose measurement, using Equation 2 below.

$$\frac{\text{Sum of amplitude absolute values in a specific frequency domain}}{\text{Sum of amplitude absolute values over the entire frequency domain}} \leq \text{Second reference value} \quad (2)$$

When a ratio of the sum of amplitude absolute values in a specific frequency domain and the sum of amplitude absolute values over the entire frequency domain is equal to or smaller than a second reference value, as shown in Equation 2, the processor 320 may determine that the plurality of skin spectra used to generate the plot of difference degree of spectra are appropriate for blood glucose measurement. In this case, the specific frequency domain is 0-0.1π, 0-0.15π, 0-0.2π, or the like, but is not limited thereto. The determination as to whether the ratio of the sum of amplitude absolute values in a specific frequency domain and the sum of amplitude absolute values over the entire frequency domain is equal to or smaller than the second reference value is based on the consideration that the specific frequency domain, such as 0-0.1π, 0-0.15π, 0-0.2π, or the like, corresponds to some spectra showing a high difference therebetween. That is, this is based on the consideration that the lower ratio of the specific frequency domain to the entire frequency domain indicates the lower ratio of highly different skin spectra so that the overall similarity of skin spectra is increased and hence the skin spectra may be determined as being appropriate for blood glucose measurement.

The processor 320 may determine whether the plurality of skin spectra used to generate the plot of difference degree of spectra in the frequency domain are appropriate for blood glucose measurement, using Equation 3 below, which is one example of the application of Equation 2.

$$\left( \sum_{-0.2\pi}^{0.2\pi} A \bigg/ \sum_{-\pi}^{\pi} A \right) \leq 0.845 \quad (3)$$

Equation 3 is, however, only one example of a method of calculating the ratio of the sum of amplitude absolute values in a specific frequency domain and the sum of amplitude absolute values over the entire frequency domain, and, thus, the range of the specific frequency domain or the second reference value is not limited to the range or the value specified in Equation 3.

When it is determined that the plurality of skin spectra used to generate the plot of difference degree of spectra are inappropriate for blood glucose measurement, the processor 320 may re-determine whether some of the skin spectra determined as being inappropriate are appropriate for blood glucose measurement, thereby finding a specific skin spectrum appropriate for the blood glucose measurement. In another example, an additional skin spectrum is acquired using the obtainer 310, and the processor 320 may find a specific skin spectrum appropriate for blood glucose measurement using a method of determining whether the acquired skin spectrum is appropriate for the blood glucose measurement.

In addition, the processor 320 may determine whether the skin spectrum determined as being appropriate for blood glucose measurement is appropriate for generation of a NAS model. The determination is based on the consideration that a NAS model generated using the skin spectra showing a high similarity therebetween has an increased accuracy or reliability.

Figure 4:
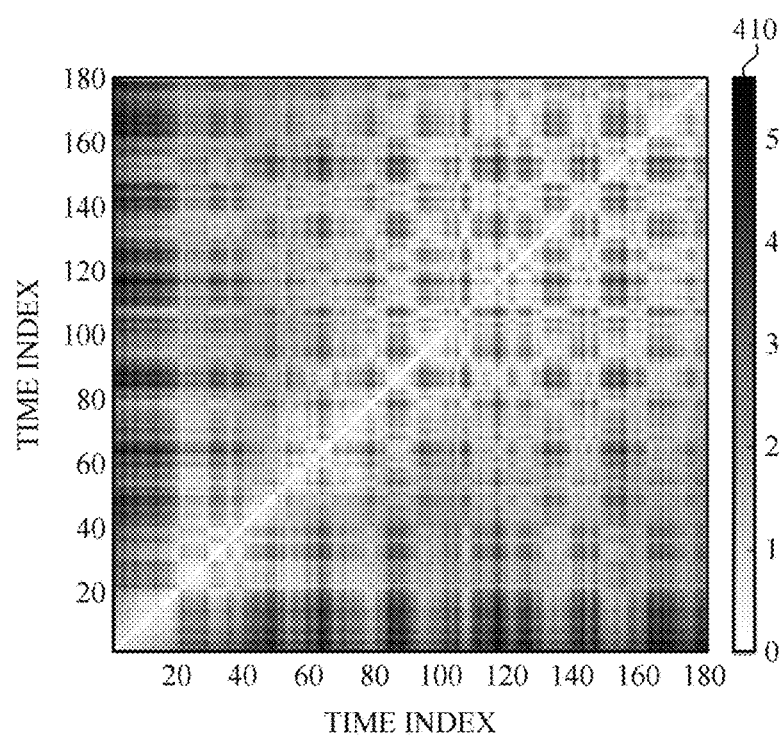
FIG. 4 is a graph illustrating an example of a plot of difference degree of spectra in time domain in the case of skin spectra showing a high overall similarity.
Figure 5:
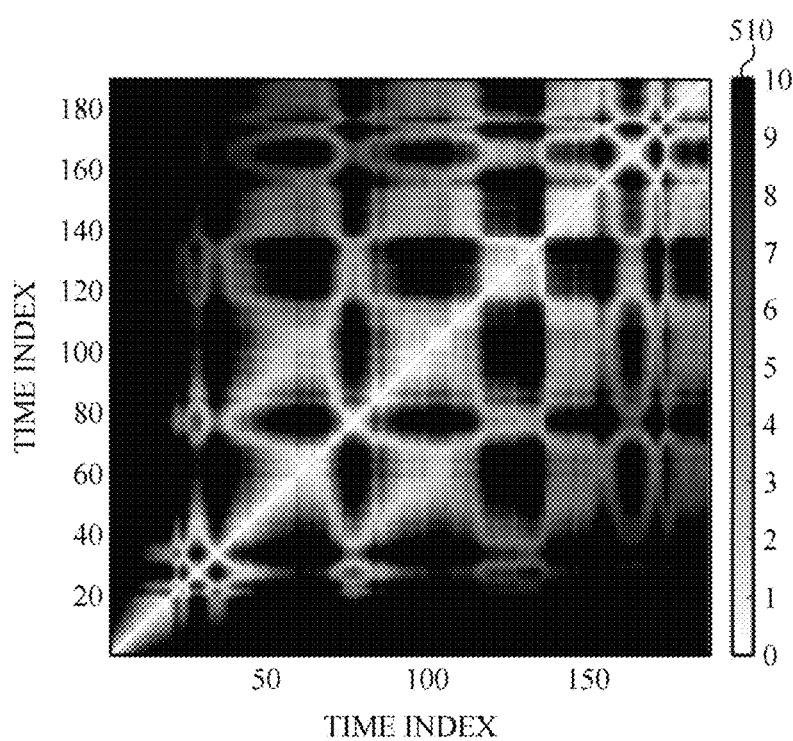
FIG. 5 is a graph illustrating an example of a plot of difference degree of spectra in time in the case of skin spectra showing a low overall similarity.

FIG. 4 is a graph illustrating an example of a plot of difference degree of spectra in time domain in the case of skin spectra showing a high overall similarity, and FIG. 5 is a graph illustrating an example of a plot of difference degree of spectra in time in the case of skin spectra showing a low overall similarity.

It is seen that the plot of difference degree of spectra of FIG. 5 has more dark regions than the plot of difference degree of spectra of FIG. 4, based on which it may be determined that a difference degree of the skin spectra used to generate the plot shown in FIG. 5 is greater than a difference degree of the skin spectra used to generated the plot shown in FIG. 4. That is, it may be understood that the overall similarity of skin spectra of FIG. 4 is greater than the overall similarity of skin spectra of FIG. 5.

Gradient brightness bars 410 and 510 shown on the right side in each of FIGS. 4 and 5 show brightness that corresponds to a range of noise values (e.g., 0 to 5 or 0 to 10) between the skin spectra. According to an exemplary embodiment, for visualization, noise values which exceed a specific value (e.g., noise values of 5 or higher in FIG. 4 or noise values of 10 or higher in FIG. 5) may be represented by the same brightness. According to another exemplary embodiment, the noise values between the skin spectra may be represented by different saturations or colors in the plot of difference degree of spectra (e.g., a higher noise value may be represented by a blue color and a lower noise value may be represented by a red color).

A white diagonal line (y=x) in each of the plots of difference degree of spectra of FIGS. 4 and 5 indicates a noise value of 0 which is calculated based on a difference between skin spectra measured at the same time (i.e., the same skin spectra).

Figure 6:
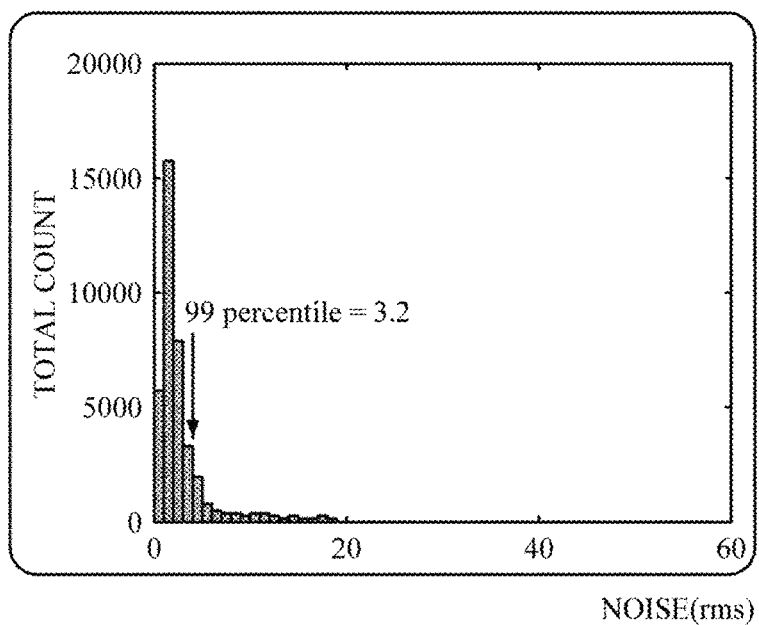
FIG. 6 illustrates an example of a noise distribution graph in the case of skin spectra showing a high overall similarity.
Figure 7:
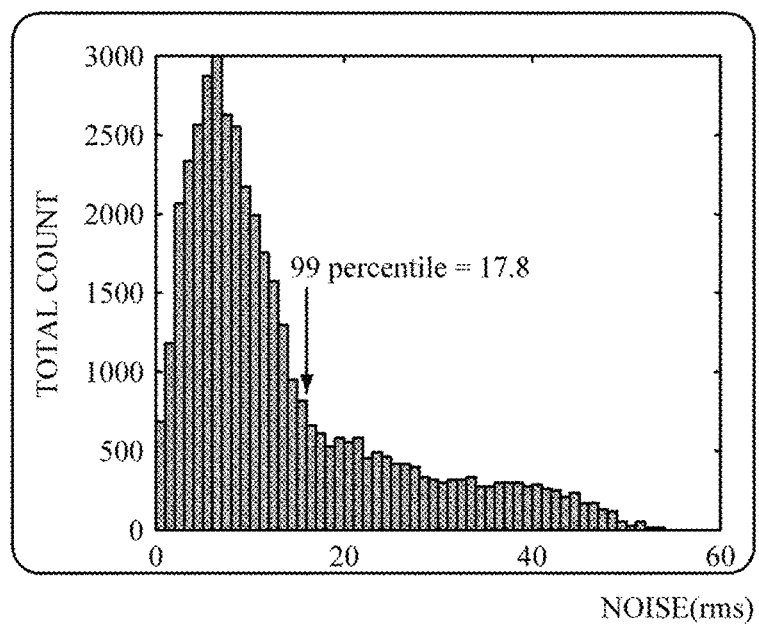
FIG. 7 illustrates an example of a noise distribution graph in the case of skin spectra showing a low overall similarity.

FIG. 6 illustrates an example of a noise distribution graph in the case of skin spectra showing a high overall similarity, and FIG. 7 illustrates an example of a noise distribution graph in the case of skin spectra showing a low overall similarity.

The noise distribution graphs of FIGS. 6 and 7 show the total number of points at which the same noise values appear in the plot of difference degree of spectra.

Referring to FIGS. 6 and 7, it is viewed that the graph of FIG. 7 has more high noise values, compared to the graph of FIG. 6, based on which it may be determined that the overall similarity of skin spectra in the case of FIG. 6 is higher than the overall similarity in the case of FIG. 7. Also, it may be determined that a more accurate result of blood glucose measurement will be obtained when using the skin spectra used to generate the noise distribution graph of FIG. 6 than when using the skin spectra used to generate the noise distribution graph of FIG. 7.

Referring to FIGS. 6 and 7, a noise value that corresponds to a 99 percentile in the noise distribution graph of FIG. 6 is 3.2, and a noise value that corresponds to a 99 percentile in the noise distribution graph of FIG. 7 is 17.8. Because the percentile score of FIG. 6 is smaller than the percentile score of FIG. 7, the processor 320 may determine that the overall similarity of the skin spectra used to generate the noise distribution graph of FIG. 6 is higher than the overall similarity of the skin spectra used to generate the noise distribution graph of FIG. 7.

When an extracted percentile score is equal to or lower than the first reference value, the processor 320 may determine that the relevant skin spectra used to generate the noise distribution graph are appropriate for blood glucose measurement. If the first reference value is set to "10" according to an exemplary embodiment, the processor 320 may determine that the skin spectra used to generate the noise distribution graph of FIG. 6 are appropriate for blood glucose measurement since a 99 percentile score of FIG. 6 is equal to or smaller than the first reference value. A 99 percentile score of FIG. 7 exceeds the first reference value, and thus, the processor 320 may determine that the skin spectra used to generate the noise distribution graph of FIG. 7 are inappropriate for blood glucose measurement.

Figure 8:
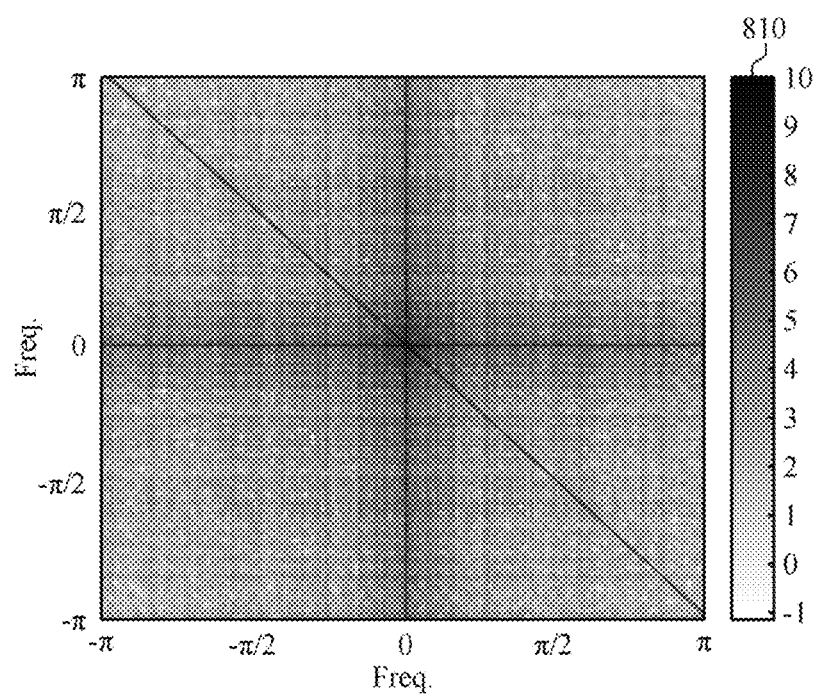
FIG. 8 is a graph illustrating an example of a plot of difference degree of spectra in frequency domain in the case of skin spectra showing a high overall similarity.
Figure 9:
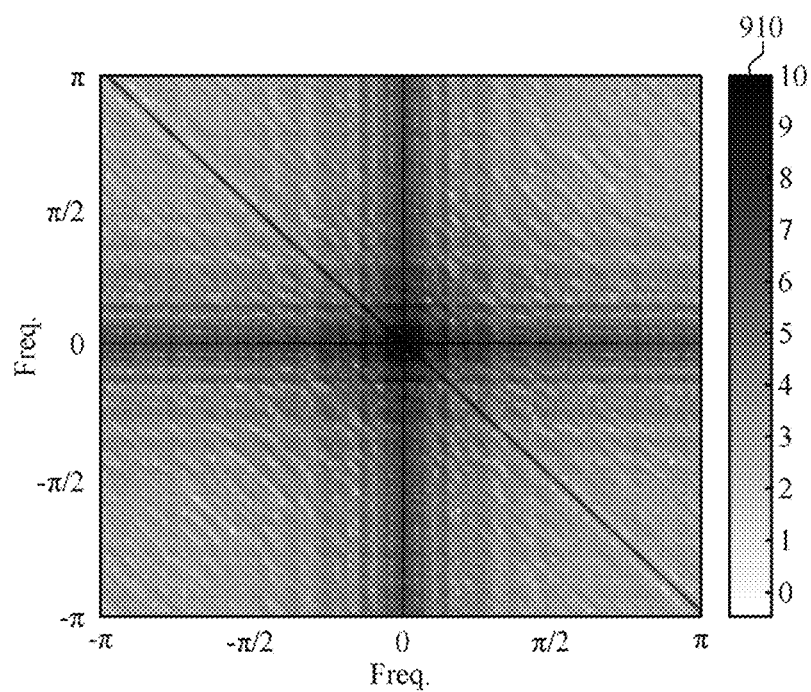
FIG. 9 is a graph illustrating an example of a plot of difference degree of spectra in frequency domain in the case of skin spectra showing a low overall similarity.

FIG. 8 is a graph illustrating an example of a plot of difference degree of spectra in frequency domain in the case of skin spectra showing a high overall similarity, and FIG. 9 is a graph illustrating an example of a plot of difference degree of spectra in frequency domain in the case of skin spectra showing a low overall similarity.

Gradient brightness bars 810 and 910 shown on the right side in each of FIGS. 8 and 9 represent the brightness that corresponds to a range of amplitude (e.g., −1 to 10 or 0 to 10) in frequency domain. According to an exemplary embodiment, for visualization, amplitudes exceeding a specific value in frequency domain (e.g., amplitudes of 10 or higher) may be represented by the same brightness. That is, lower brightness indicates higher amplitude. Thus, based on the observation that a specific frequency domain (e.g., a range close to the frequency value of 0) in the plot of difference degree of spectra of FIG. 9 is represented by darker shade, when compared with the plot of difference degree of spectra of FIG. 8, it may be determined that the overall similarity of the skin spectra used to generate the plot of difference degree of spectra of FIG. 8 is higher than the overall similarity of the skin spectra used to generate the plot of difference degree of spectra of FIG. 9.

Figure 10:
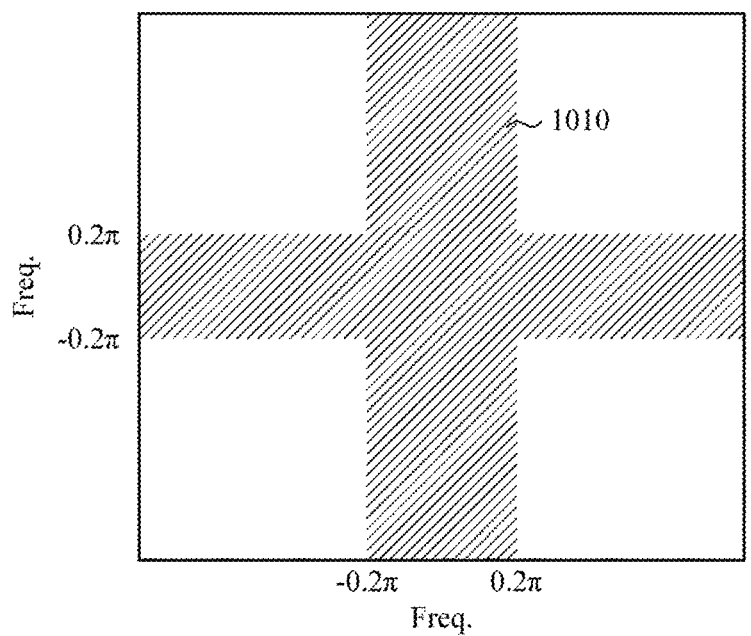
FIG. 10 is a diagram illustrating an example of a specific frequency domain in a plot of difference degree of spectra in frequency domain.

FIG. 10 is a diagram illustrating an example of a specific frequency domain in a plot of difference degree of spectra in frequency domain.

As described above, when a ratio of the sum of amplitude absolute values in a specific frequency domain and the sum of amplitude absolute values over the entire frequency domain is equal to or smaller than the second reference value, the processor 320 may determine that the plurality of skin spectra used to generate the plot of difference degree of spectra are appropriate for blood glucose measurement. FIG. 10 shows the specific frequency domain (−2π to 2π) specified by Equation 3 above. However, as described above, the specific frequency domain is not limited to the above description of FIG. 10 and Equation 3.

FIG. 10 illustrates the case in which analysis is performed using all quadrants of the plot of difference degree of spectra. However, the analysis may be performed on any one of the quadrants since the four quadrants of the plot of difference degree of spectra in the frequency domain are symmetrical with respect to one another.

Figure 11:
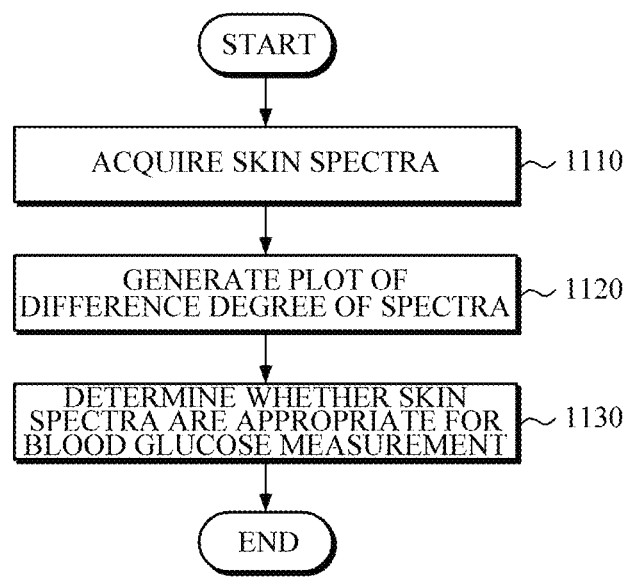
FIG. 11 is a flowchart illustrating a method of spectrum analysis according to an exemplary embodiment.

FIG. 11 is a flowchart illustrating a method of spectrum analysis according to an exemplary embodiment.

Referring to FIGS. 3 and 11, the device 300 for spectrum analysis acquires a plurality of skin spectra in operation 1110. The device 300 may acquire the skin spectra through a spectroscope or obtain the skin spectra from a record device through a wired/wireless communication device.

The device 300 generates a plot of difference degree of spectra which represents differences among the acquired plurality of skin spectra, in operation 1120. More specifically, the device 300 may calculate a noise value between every two of the plurality of skin spectra and generate the plot of difference degree of spectra using the calculated noise values.

The device 300 quantitatively analyzes the plot of difference degree of spectra and determines whether the skin spectra are appropriate for blood glucose measurement based on the analysis result, in operation 1130.

Figure 12:
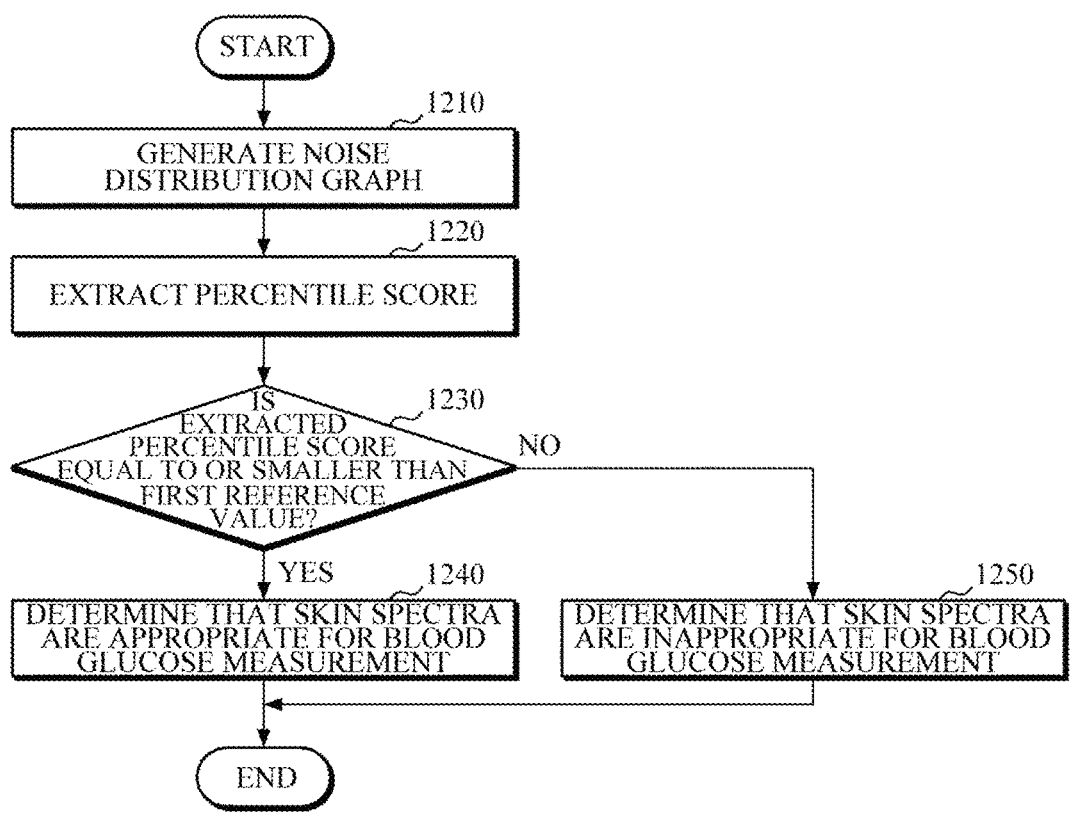
FIG. 12 is a flowchart illustrating the determination as depicted in 1130 of FIG. 11 according to an exemplary embodiment.

FIG. 12 is a flowchart illustrating the determination as depicted in 1130 of FIG. 11 according to an exemplary embodiment.

Referring to FIGS. 3 and 12, the device 300 generates a noise distribution graph based on the generated plot of difference degree of spectra in operation 1210.

The device 300 extracts a percentile score that corresponds to a specific percentile in the generated noise distribution graph, in operation 1220. For example, the device 300 may extract a noise value that corresponds to a predetermined percentile as the percentile score. In addition, the predetermined percentile may be a 95 percentile or a 99 percentile.

The device 300 compares the extracted percentile score with a first reference value, in operation 1230.

When the extracted percentile score is equal to or smaller than the first reference value, the device 300 determines that the plurality of skin spectra used to generate the noise distribution graph are appropriate for blood glucose measurement, in operation 1240.

When the extracted percentile score exceeds the first reference value, the device 300 determines that the plurality of skin spectra used to generate the noise distribution graph are inappropriate for blood glucose measurement, in operation 1250.

Figure 13:
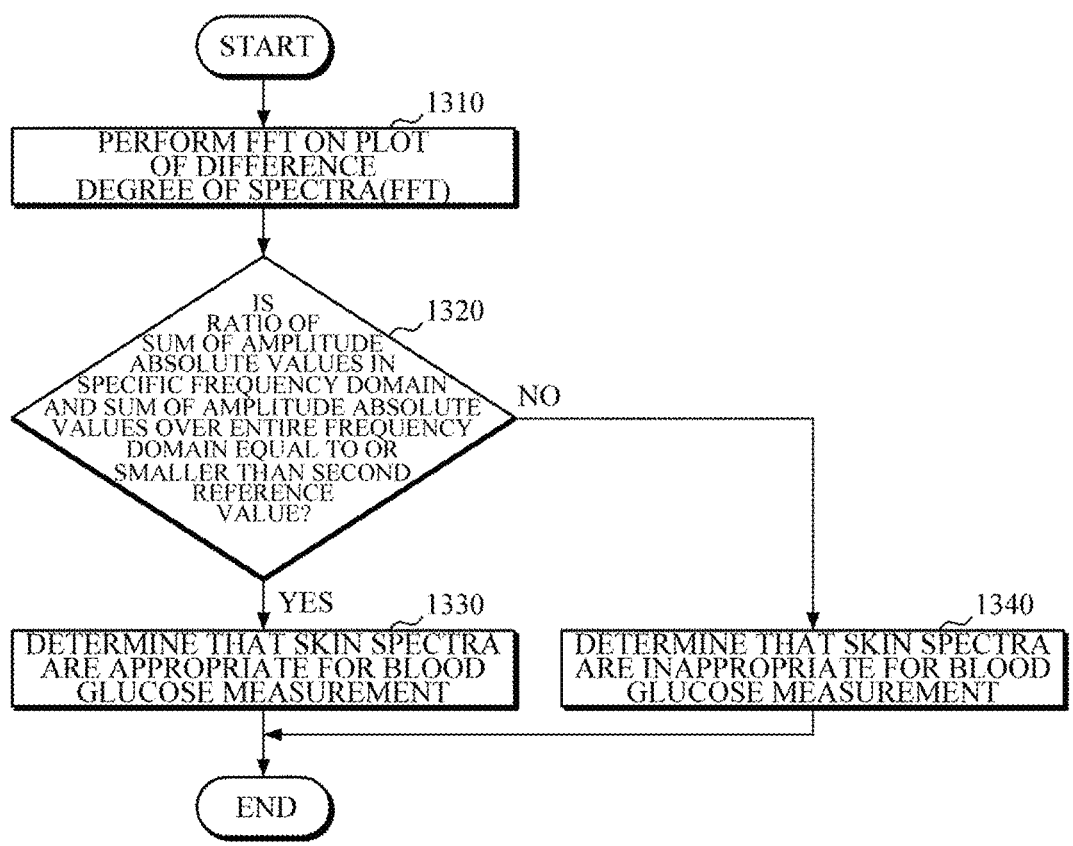
FIG. 13 is a flowchart illustrating the determination as depicted in 1130 of FIG. 11 according to another exemplary embodiment.

FIG. 13 is a flowchart illustrating the determination as depicted in 1130 of FIG. 11 according to another exemplary embodiment.

Referring to FIGS. 3 and 13, the device 300 converts the plot of difference degree of spectra in time domain into frequency domain by performing an FFT, in operation 1310.

The device 300 compares a ratio of the sum of amplitude absolute values in a specific frequency domain and the sum of amplitude absolute values over the entire frequency domain with a second reference value, in operation 1320. When the ratio of the sum of amplitude absolute values in a specific frequency domain and the sum of amplitude absolute values over the entire frequency domain is equal to or smaller than the second reference value, the device 300 determines that the plurality of skin spectra used to generate the plot of difference degree of skin spectra are appropriate for blood glucose measurement, in operation 1330, and, when the ratio exceeds the second reference value, determines that the plurality of skin spectra are inappropriate for blood glucose measurement, in operation 1340.

In addition, the device 300 or the method for spectrum analysis may be applied to the measurement of the concentration of blood components, such as cholesterol, albumin, hemoglobin, and bilirubin, and the concentration of a specific analyte, such as alcohol or drug, in a blood sample.

Figure 14:
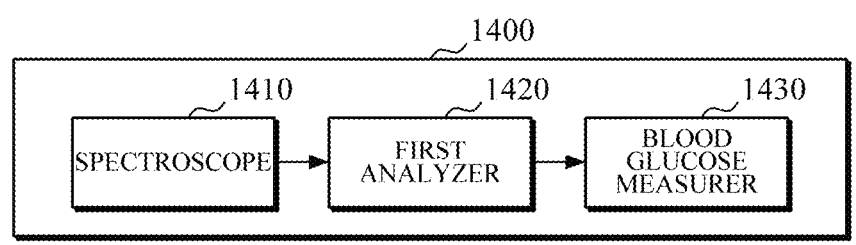
FIG. 14 is a block diagram illustrating a blood glucose measurement device according to an exemplary embodiment.

FIG. 14 is a block diagram illustrating a blood glucose measurement device according to an exemplary embodiment.

Referring to FIG. 14, the blood glucose measurement device 1400 includes a spectroscope 1410, a first analyzer 1420, and a blood glucose level measurer 1630. The first analyzer 1420 may be the device 300 for spectrum analysis of FIG. 3.

The spectroscope 1410 may emit light onto a subject, receive light reflected or scattered from the subject, and acquire a plurality of skin spectra based on the received light. The spectroscope 1410 may include a light source configured to emit light, a reflector configured to reflect the light emitted from the light source, a condenser configured to collect and condense the light to irradiate the subject, a light detector configured to receive an optical signal passing through the subject or an optical signal reflected from the subject, and an optical signal obtainer configured to convert the received optical signal into an analog electric signal or a digital signal.

The first analyzer 1420 may generate a plot of difference degree of spectra that represents differences among the plurality of skin spectra using the skin spectra obtained by the spectroscope 1410 and may analyze the plot of difference degree of spectra so as to determine whether the skin spectra are appropriate for blood glucose measurement.

According to an exemplary embodiment, the first analyzer 1420 may generate a noise distribution graph based on the plot of difference degree of spectra, extract a percentile score that corresponds to a predetermined percentile in the generated noise distribution graph, compare the first extracted percentile score with a first reference value, and determine whether the skin spectra are appropriate for blood glucose measurement, based on the comparison result.

According to another exemplary embodiment, the first analyzer 1420 may convert the plot of difference degree of spectra into frequency domain by performing an FFT, compare a ratio of the sum of amplitude absolute values in a specific frequency domain and the sum of amplitude absolute values over the entire frequency domain with a second reference value, and determine whether the skin spectra are appropriate for blood glucose measurement, based on the comparison result.

When it is determined that the plurality of skin spectra are appropriate for blood glucose measurement, the blood glucose measurer 1430 may measure the blood glucose level using the skin spectra determined as being suitable. Such measurement is based on the consideration that the blood glucose measurement which is performed using the skin spectra showing a higher similarity to one another has an increased accuracy, reliability and the like. The blood glucose measurer 1430, however, may forcibly perform blood glucose measurement using the skin spectra that are determined as being inappropriate for measurement, according to a user's setting or control.

Figure 15:
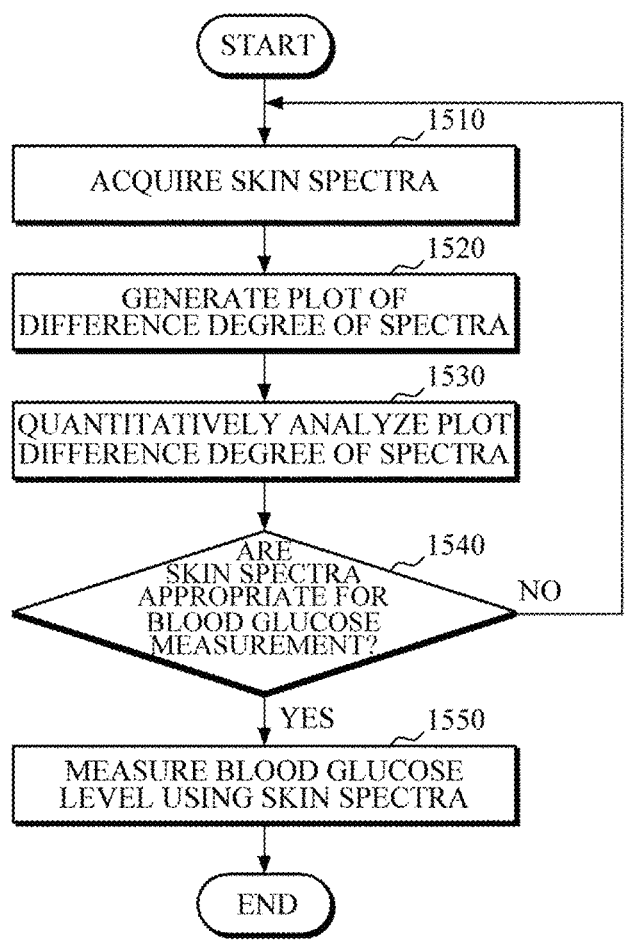
FIG. 15 is a flowchart illustrating a blood measurement method according to an exemplary embodiment.

FIG. 15 is a flowchart illustrating a blood measurement method according to an exemplary embodiment.

Referring to FIGS. 14 and 15, the blood glucose measurement device 1400 emits light onto the subject, receive light reflected or scattered from the subject, and obtain a plurality of skin spectra based on the received light, in operation 1510.

The blood glucose measurement device 1400 generates a plot of difference degree of spectra that represents differences among the skin spectra, using the obtained skin spectra, as depicted in 1520.

The blood glucose measurement device 1400 quantitatively analyzes the plot of difference degree of spectra, as depicted in 1530, and determine whether the plurality of skin spectra used to generate the plot of difference degree of spectra are appropriate for blood glucose measurement, based on the quantitative analysis result, in operation 1540.

The blood glucose measurement device 1400 performs blood glucose measurement using the acquired skin spectra, in operation 1550.

When it is determined that the acquired skin spectra are inappropriate for blood glucose measurement, the blood glucose measurement device 1400 may return to operation 1510 to acquire new skin spectra using the spectroscope.

Figure 16:
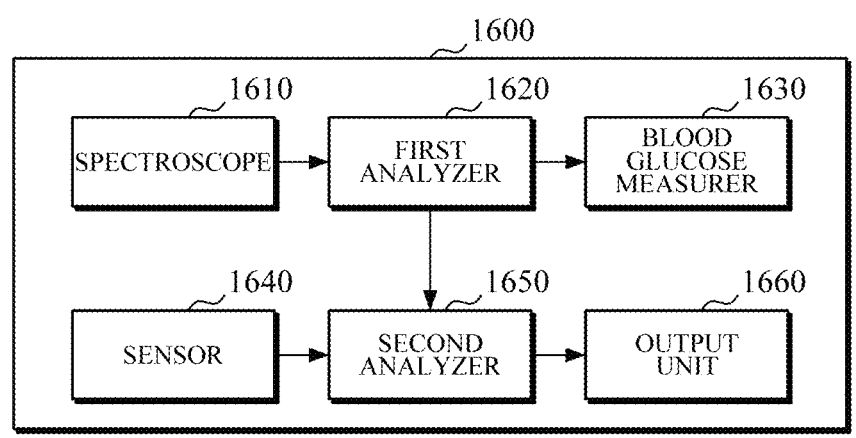
FIG. 16 is a block diagram illustrating a blood glucose measurement device according to another exemplary embodiment.

FIG. 16 is a block diagram illustrating the blood glucose measurement device according to another exemplary embodiment.

Referring to FIG. 16, the blood glucose measurement device 1600 includes a spectroscope 1610, a first analyzer 1620, a blood glucose measurer 1630, a sensor 1640, a second analyzer 1650, and an output unit 1660. The spectroscope 1610, the first analyzer 1620, and the blood glucose measurer 1630 are described with reference to FIG. 14, and hence the detailed descriptions thereof will not be repeated.

The sensor 1640 may measure an environmental index at the time of the acquisition of skin spectra. The environmental index may be a numerical value that represents a state of the blood glucose measurement device 1600 or the surrounding environment thereof during the acquisition of the skin spectra. For example, the environment index may include a temperature, a humidity, a degree of motion of the blood glucose measurement device 1600, and so on.

In this case, the degree of motion of the blood glucose measurement device 1600 may include a value obtained by quantifying detected vibration of the blood glucose measurement device 1600, a value obtained by quantifying a change in location information of the blood glucose measurement device 1600, and the like.

The second analyzer 1650 may analyze the correlation between the environmental index and the overall similarity of skin spectra. For example, if, as the subject is wet with water and humidity is raised during the acquisition of skin spectrum, the difference between the overall similarity of skin spectra and the reference value for determining whether to use the skin spectra in blood glucose measurement is increased, the second analyzer 1650 may determine that the humidity at the time of the acquisition of skin spectra is a factor that affects similarities among the skin spectra and may determine that the humidity and the similarities among the skin spectra are in negative correlation. In the same manner, the second analyzer 1650 may analyze the correlation with other environmental indices and the overall similarity of skin spectra.

During the additional acquisition of skin spectra, the output unit 1660 may output a predetermined warning signal when an environmental index having a positive correlation with the overall similarity of skin spectra is equal to or smaller than a third reference value, or when an environmental index having a negative correlation with the overall similarity of skin spectra is equal to or greater than a fourth reference value, that is, when the blood glucose measurement device 1600 is acquiring the skin spectra in an environment in which the overall similarity of skin spectra is likely to be low. For example, the output unit 1660 may be an imaging device, such as a display, which outputs a visual signal as a warning message to a screen, an acoustic device, such as a speaker or earphones, which outputs an audible signal as a warning sound, or a vibration device which vibrates in a specific manner.

Figure 17:
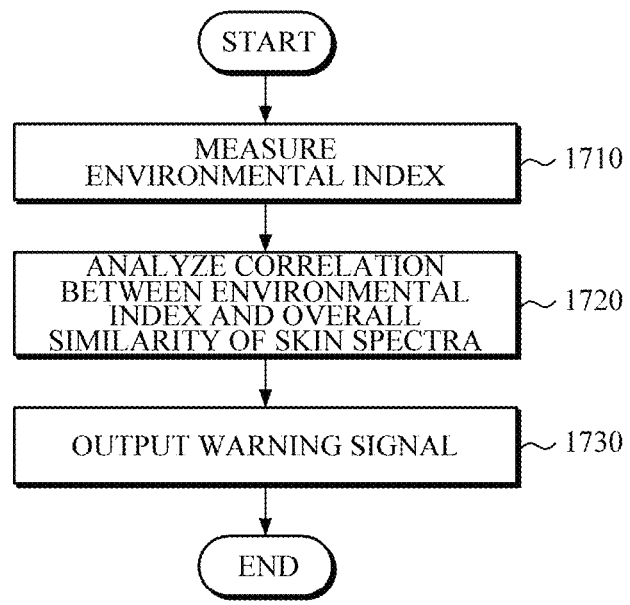
FIG. 17 is a flowchart illustrating a blood glucose measurement method according to another exemplary embodiment.

FIG. 17 is a flowchart illustrating a blood glucose measurement method according to another exemplary embodiment.

Referring to FIGS. 16 and 17, the blood glucose measurement device 1600 measures an environmental index at the time of the acquisition of skin spectra in operation 1710, wherein the environmental index includes at least one of a temperature, humidity and a degree of motion of the blood glucose measurement device during the acquisition of the skin spectra.

The blood glucose measurement device 1600 analyzes a correlation between the environmental index and the overall similarity of skin spectra, in operation 1720.

While the blood glucose measurement device 1600 is acquiring additional skin spectra, the blood glucose measurement device 1600 may output a predetermined warning signal when an environmental index having a positive correlation with the overall similarity of skin spectra is equal to or smaller than a third reference value, or when an environmental index having a negative correlation with the overall similarity of skin spectra is equal to or greater than a fourth reference value, in operation 1730, wherein the warning signal may be a visual signal, an audible signal, or a vibration signal, as described above.

The current exemplary embodiments can be implemented as computer readable codes stored in a computer readable recording medium and executed by computer or processor. Codes and code segments constituting the computer program can be easily inferred by a skilled computer programmer in the art. The computer readable recording medium may include all types of recording media in which computer readable data are stored. Examples of the computer readable recording medium include a ROM, a RAM, a CD-ROM, a magnetic tape, a floppy disk, and an optical data storage. Further, the recording medium may be implemented in the form of a carrier wave such as Internet transmission. In addition, the computer readable recording medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A device for blood glucose measurement, the device comprising:

a spectroscope configured to emit light onto a subject and acquire a plurality of skin spectra based on light passing through or reflected from the subject;

a first analyzer configured to:

generate a plot of difference degree of spectra which represents differences among the acquired plurality of skin spectra;

quantify an overall similarity between the plurality of skin spectra by quantitatively analyzing the plot of difference degree of spectra; and determine whether the plurality of skin spectra are appropriate for blood glucose measurement based on the quantified overall similarity being equal to or greater than a threshold; and a blood glucose measurer configured to perform blood glucose measurement using skin spectra which are determined by the first analyzer as being appropriate for blood glucose measurement.

2. The device of claim 1, wherein the first analyzer is further configured to generate a noise distribution graph based on the plot of difference degree of spectra, determine a percentile score that corresponds to a predetermined percentile in the noise distribution graph, and compare the percentile score with a reference value to determine whether the plurality of skin spectra are appropriate for blood glucose measurement.

3. The device of claim 2, wherein the first analyzer is further configured to determine that the plurality of skin spectra are appropriate for blood glucose measurement based on the percentile score being less than or equal to the reference value.

4. The device of claim 1, wherein the first analyzer is further configured to convert the plot of difference degree of spectra into frequency domain by performing a fast Fourier transform (FFT) and determine whether the plurality of skin spectra are appropriate for blood glucose measurement by comparing a reference value with a ratio of a sum of amplitude absolute values in a predetermined frequency domain of the converted plot of difference degree of spectra and a sum of amplitude absolute values over an entire frequency domain.

5. The device of claim 4, wherein the first analyzer is further configured to determine that the plurality of skin spectra are appropriate for blood glucose measurement based on the ratio of the sum of amplitude absolute values in a predetermined frequency domain and the sum of amplitude absolute values over an entire frequency domain being equal to or smaller than the reference value.

6. The device of claim 1, wherein the first analyzer is further configured to determine a noise value by performing baseline fitting on two spectra and then integrating a difference in frequency intensity between the two spectra, and generate the plot of difference degree of spectra based on the noise value.

7. The device of claim 1, wherein the spectroscope is further configured to emit near-infrared light and acquire near-infrared extinction spectrum absorbed by the subject.

8. The device of claim 1, further comprising:
a sensor configured to measure an environmental index including at least one of a temperature, a humidity and a degree of motion of the device for blood glucose measurement during the acquisition of the skin spectra;
a second analyzer configured to analyze a correlation between the environmental index and an overall similarity of skin spectra; and
an output unit configured to output a predetermined warning signal during additional acquisition of a skin spectrum based on an environmental index having a positive correlation with the overall similarity of skin spectra being less than or equal to a first reference value, or based on an environmental index having a negative correlation with the overall similarity of skin spectra being greater than or equal to a second reference value.

9. The device of claim 1, wherein the spectroscope is further configured to acquire an additional skin spectrum based on determination that the plurality of skin spectra are inappropriate for blood glucose measurement.

10. A device for blood glucose measurement, the device comprising:
a spectroscope configured to emit light onto a subject and acquire a plurality of skin spectra based on light passing through or reflected from the subject;
a first analyzer configured to generate a plot of difference degree of spectra which represents differences among the acquired plurality of skin spectra, and determine whether the plurality of skin spectra are appropriate for blood glucose measurement based on the plot of difference degree of spectra; and
a blood glucose measurer configured to perform blood glucose measurement using skin spectra which are determined by the first analyzer as being appropriate for blood glucose measurement,
wherein the first analyzer is further configured to determine a noise value by performing baseline fitting on two spectra and then integrating a difference in frequency intensity between the two spectra, and generate the plot of difference degree of spectra based on the noise value.

11. A device for blood glucose measurement, the device comprising:
a spectroscope configured to emit light onto a subject and acquire a plurality of skin spectra based on light passing through or reflected from the subject;
a first analyzer configured to generate a plot of difference degree of spectra which represents differences among the acquired plurality of skin spectra, convert the plot of difference degree of spectra into frequency domain by performing a fast Fourier transform (FFT), and determine whether the plurality of skin spectra are appropriate for blood glucose measurement based on the converted plot of difference degree of spectra; and
a blood glucose measurer configured to perform blood glucose measurement using skin spectra which are determined by the first analyzer as being appropriate for blood glucose measurement.

* * * * *